United States Patent [19]

Tepic et al.

[11] Patent Number: 5,211,664
[45] Date of Patent: May 18, 1993

[54] SHELL STRUCTURE FOR BONE REPLACEMENT

[75] Inventors: Slobodan Tepic; Stephen J. Bresina, both of Davos; Sylwester Gogolewski, Alvaneu-Dorf, all of Switzerland

[73] Assignee: Forschungsinstitut, Davos Laboratorium fur Experimentelle Chirugie, Davos, Switzerland

[21] Appl. No.: 820,758

[22] Filed: Jan. 14, 1992

[51] Int. Cl.$^5$ ............................. A61F 2/28; A61F 2/54
[52] U.S. Cl. ........................................ 623/16; 623/66; 606/60
[58] Field of Search ................ 623/16, 22, 23, 66, 623/18, 17; 606/20, 72, 74, 60, 62, 73

[56] References Cited

U.S. PATENT DOCUMENTS

| | | | |
|---|---|---|---|
| 4,708,652 | 11/1987 | Fujiu et al. | 623/18 X |
| 4,843,112 | 6/1989 | Gerhart et al. | 623/16 X |
| 4,938,768 | 7/1990 | Wu | 606/60 |
| 4,960,426 | 10/1990 | Atsumi et al. | 623/16 X |
| 4,990,161 | 2/1991 | Kampner | 623/16 |
| 4,990,163 | 2/1991 | Ducheyne et al. | 623/16 X |
| 5,021,063 | 6/1991 | Tager et al. | 623/22 X |
| 5,032,134 | 7/1991 | Lindwer | 623/23 |
| 5,034,352 | 7/1991 | Vit et al. | 623/16 X |
| 5,061,286 | 10/1991 | Lyle | 623/16 |
| 5,067,963 | 11/1991 | Khouri et al. | 623/16 |
| 5,073,114 | 12/1991 | Detsch | 623/16 X |

Primary Examiner—Randall L. Green
Assistant Examiner—Dinh X. Nguyen
Attorney, Agent, or Firm—McAulay, Fisher, Nissen, Goldberg & Kiel

[57] ABSTRACT

Bone defects after trauma, tumor resection, etc. still present a major clinical problem. Current treatment with bone grafts, bone-inducing substances, Ilizarov techniques, artificial prosthetic replacements, or bone transplants are only partially satisfying. Bioresorbable shell structures for treatment of bone defects are disclosed. The shells are anatomically shaped and serve as containers or bone grafts or bone precursors as well as temporary structural supports. The shells are preferably porous allowing for nutritional support of the graft and limit the thickness of the graft to no more than a few millimeters. Thus nutrients and metabolic by-products transport by diffusion alone is sufficient to maintain grafted metabolism in the critical phase before revascularization takes place.

18 Claims, 7 Drawing Sheets

SHELL STRUCTURE FOR BONE REPLACEMENT

BACKGROUND OF THE INVENTION

1. Field of the Invention

The invention relates to a shell structure for living tissue replacement, particularly replacement of segments of long bones.

2. Description of the Prior Art

Large bone defects may be caused by severe trauma, by treatment complications (infection), or by the removal of bone tumors. There are several methods currently used for treatment of such defects. The methods of bone segment transport—as developed by ILIZAROV—produce new bone by distracting a zone of tissue growth. This works very well for diaphyseal defects, where the bone geometry is simple and generally cylindrical. The treatment lasts rather long (1 mm per day plus consolidation time of several weeks to several months) and requires an external frame.

Another method is to replace the defect with an artificial permanent implant, i.e. a prosthesis. These prosthesis are made from metals, plastics, ceramics or combinations of these. They serve the purpose of structural support, but usually lead to long term complications. With improved treatments of bone tumors, patients, life expectancy is likely to exceed life expectancy of currently used prosthesis. Another method used for treatment of large defects, especially those involving complex anatomical structures such as joints, is transplantation. Similar to blood banks, bone banks exist to provide a supply of bones for allografts. Typically, the transplant is dead and is never revitalized passed a short distance from the interface to the host tissue. Long term success of the transplants is very low.

Autografting of bone defects with cancellous bone material is the most widely used technique. The availability of the material is limited and the current practice is extremely inefficient in using the graft. Typically the grafting bone is crushed into small pieces (collected mainly from pelvic bone) and laid into the defect. In a major bone the volume of the defect is large and the graft is initially without a viable vascular supply. Large volumes cannot be supported by nutrients from the surrounding tissue and most of the graft cells die leading to a large volume of necrotic tissue which presents a major burden to the immune system. These grafts have at best been contained to their intended location by wrapping into either appropriate natural tissues or artificial membranes.

All these methods have failed in producing predictable replacement of living tissue and are only partially satisfying.

SUMMARY OF THE INVENTION

The invention as claimed is intended to remedy these drawbacks. It solves the problem of how to design a shell structure for living tissue replacement.

The invention solves the problem with a shell structure comprising an inner tubular shell positioned within an outer tubular shell forming a hollow cylindrical volume therebetween, designed to receive segments of a bone to be connected. Struts disposed within the volume connect the inner and outer shells. The inner surface of the outer shell fits over the outer surfaces of the bone segments being connected. The hollow volume is open at each end of the structure. The structure is constructed from resorbable or degradable polymeric and/or polymeric ceramic material having an overall porosity below 90% and a method for producing a shell structure comprising (a) collecting geometrical data of the bone to be replaced;

(b) building a hollow cylindrical model from a water soluable model having a number of holes connecting the outer and inner surfaces of the model;

(c) coating the model with a number of layers of resorbable or degradable polymeric and/or polymeric ceramic material to form an outer shell and inner shell connected to a number of struts;

(d) dissolving the water soluable model, leaving the tubular shell structure ready for use.

Bioresorbable shell structures according to this invention offer a significant improvement for treatment of bone defects. The shell structures are anatomically shaped and serve as containers or bone grafts or bone precursors as well as temporary structural supports.

The material to be used for the shell structure is preferably a bioresorbable or degradable polymeric and/or polymeric-ceramic material. It comprises preferably highly purified polyhydroxyacids, polysaccharides, polyamines, polyaminoacids, polyorthoesters, polyanhydrides, collagen or composites thereof with tricalcium phosphate and/or hydroxyapatite, or bioresorbable glasses.

With existing biomaterials it is further possible to construct the shell structure so as to match not only the shape of the bone to be reconstructed, but also its mechanical properties.

If the mechanical properties of the missing bone are to be matched, a reinforced, bioresorbable polymer is the preferred choice. The reinforcement material can be resorbable and/or degradable fibre, for example bioglass fibre and the matrix material polylactide. Bioresorbable ceramics can be used as both the reinforcement and matrix material.

In a preferred embodiment of the invention at least one, and preferably both, of the shells forming the shell structure are microporous allowing for nutritional support of the graft and limiting the thickness of the graft to no more than a few millimeters. Thus nutrients and metabolic by-products transport by diffusion alone is sufficient to maintain grafted metabolism in the critical phase before revascularisation takes place.

The specific pore size, shape and structure to be selected for a certain application is variable over a large extent, whereby the overall porosity is below 90%. Preferably at least 90 percent of the micropores present in the polymeric material should have a diameter below 500 $\mu$m, preferably in the range of 0.01 to 50.0 $\mu$m and most preferably in the range of 0.1 to 5 $\mu$m. What is essential is that the micropores are permeable for nutritional fluids. Therefore the micropores within the shell wall must be interconnected to allow liquids penetration and circulation.

In a further preferred embodiment of the invention at least one of the inner and outer shell is provided with larger openings in the range of 0.1 to 2.0 mm.

In general, the shell structure is produced to closely match the anatomy of the defect, with the void space within the shell structure corresponding to the cortical bone of the defect. To this effect the spacing between the inner and outer shell is in the range of 0.1 to 10.0 mm, preferably in the range of 1.0 to 5.0 mm.

The walls of the inner and outer shell have a thickness of between 0.05 to 5.0 mm, preferably between 0,2 to 3.0 mm, most preferably between 0.4 to 1.5 mm.

The space between the inner and outer shell forms a new artificial cortex that can be filled with a variety of therapeutic substances, such as autologous bone, allogenic bone, demineralized bone powder extracts, bone morphogenetic protein isolates, osteogenin, antibiotics, or antineoplastic drugs.

The various features of novelty which characterize the invention are pointed out with particularity in the claims annexed to and forming part of this disclosure. For the better understanding of the invention, its operating advantages and specific objects attained by its use, reference should be had to the accompanying drawings, examples and descriptive matter in which are illustrated and described preferred embodiments of the invention.

BRIEF DESCRIPTION OF THE DRAWINGS

FIG. 5b shows a cross section of the shell structure corresponding to the cross section of FIG. 5a;

DESCRIPTION OF THE PREFERRED EMBODIMENTS

Figure 1:
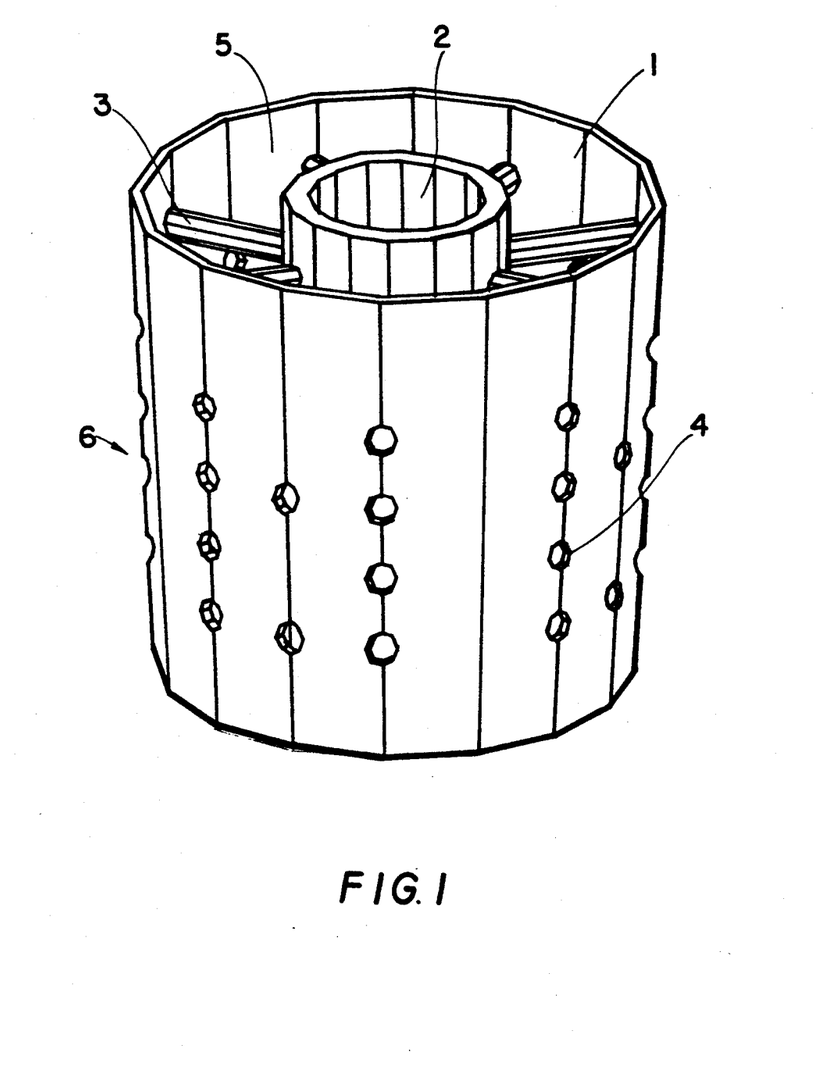
FIG. 1 is a perspective view of the shell structure of the present invention.

FIG. 1 shows the main features of a shell structure 6 according to the invention which here is shaped to be used for a mid segment (diaphyseal) defect of a long bone.

The shell structure 6 has an outer shell 1 and an inner shell 2. These are connected by a number of struts 3. Both of the shells 1 and 2 are microporous allowing for diffusion of nutrients and metabolic products. Porosity should be at least 20% of the the total material volume and preferably 50% of the the total material volume. The diameter of the pores should be in the range of 5 to 100 μm and preferably of 15–50 μm.

In addition to the micropores, the inner and outer shell 1 and 2 have some larger openings 4 with a diameter of 1 to 2 mm, which allow for vascular ingrowth from the surrounding tissue.

The distance between the two shells in this example corresponds to cortical thickness of 6 to 8 mm.

Figure 2:
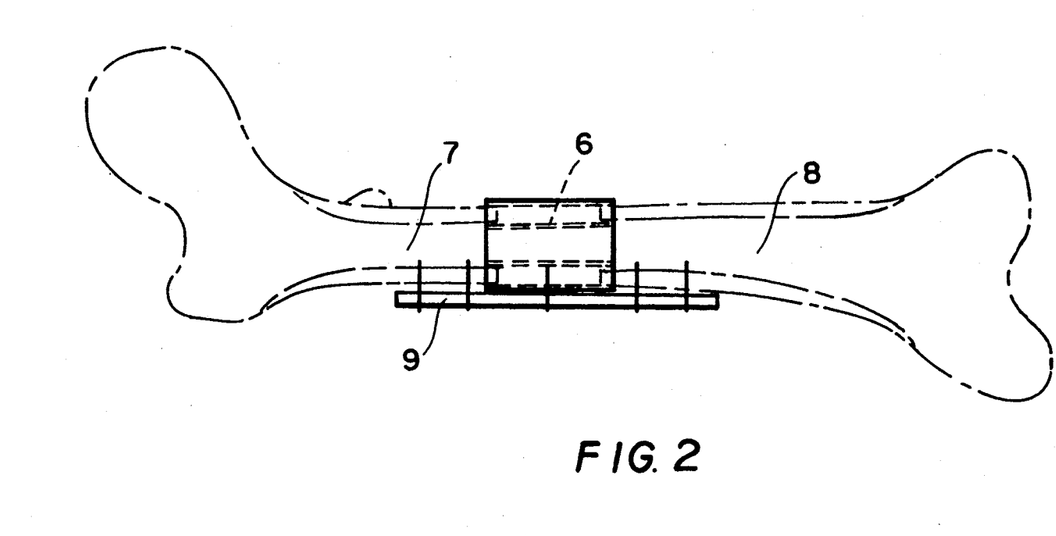
FIG. 2 is a schematic representation of how the shell structure of FIG. 1 is fixed in place between bone fragments by a bone plate.

The void space 5 between the shells 1 and 2 is filled with the bone graft or the bone precursor and the shell structure 6 is inserted to fill the bone defect as shown on FIG. 2.

According to FIG. 2 the shell structure 6 can be fixed in place between bone segments 7 and 8 by means of a bone plate 9.

Figure 3:
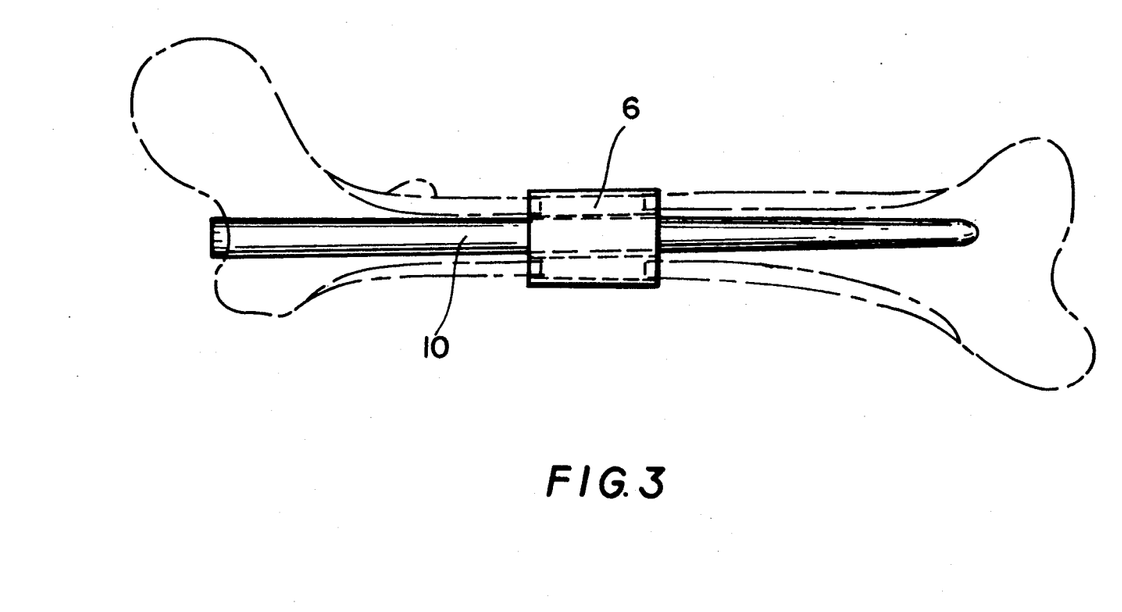
FIG. 3 is a schematic representation of how the shell structure of FIG. 1 is fixed in place between bone fragments by an intramedullary nail.

Alternatively, as shown in FIG. 3, an intramedullary nail 10 can be used as means of fixation for the shell structure 6.

Figure 4:
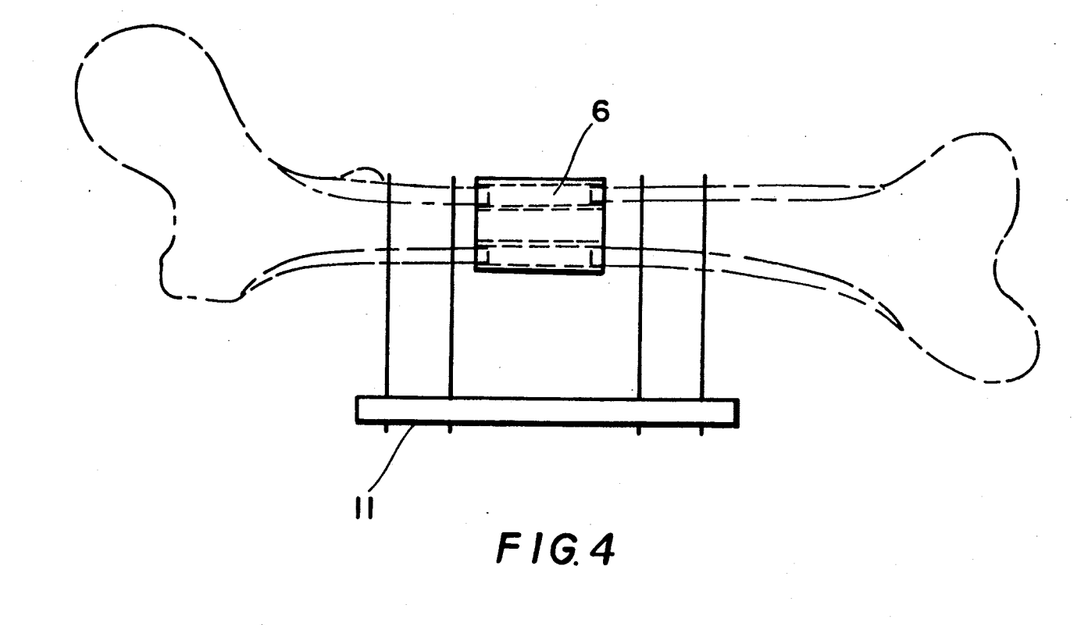
FIG. 4 is a schematic representation of how the shell structure of FIG. 1 is fixed in place between bone fragments by an external frame.

The use of an external frame 11, as shown in FIG. 4, for fixation of the shell structure 6 is least favourable due to high compliance—but still viable—for the purpose.

Figure 5A:
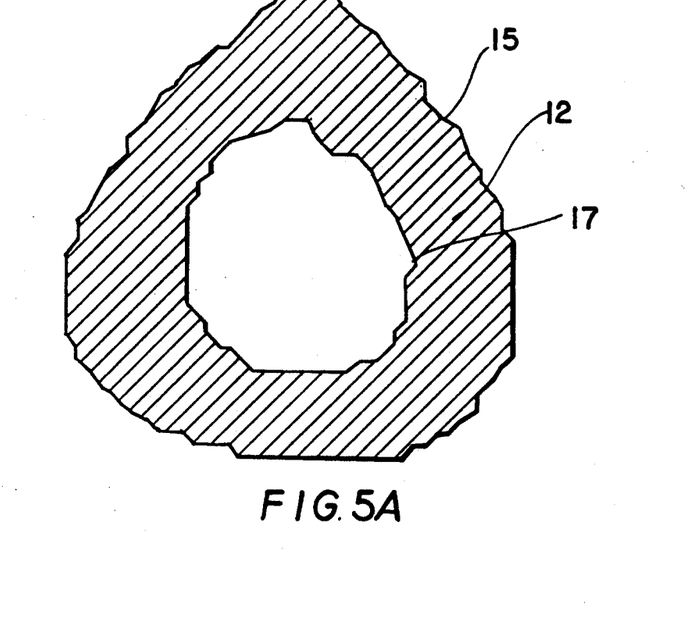
FIG. 5a shows a cross section of a femur bone 12.
Figure 5B:
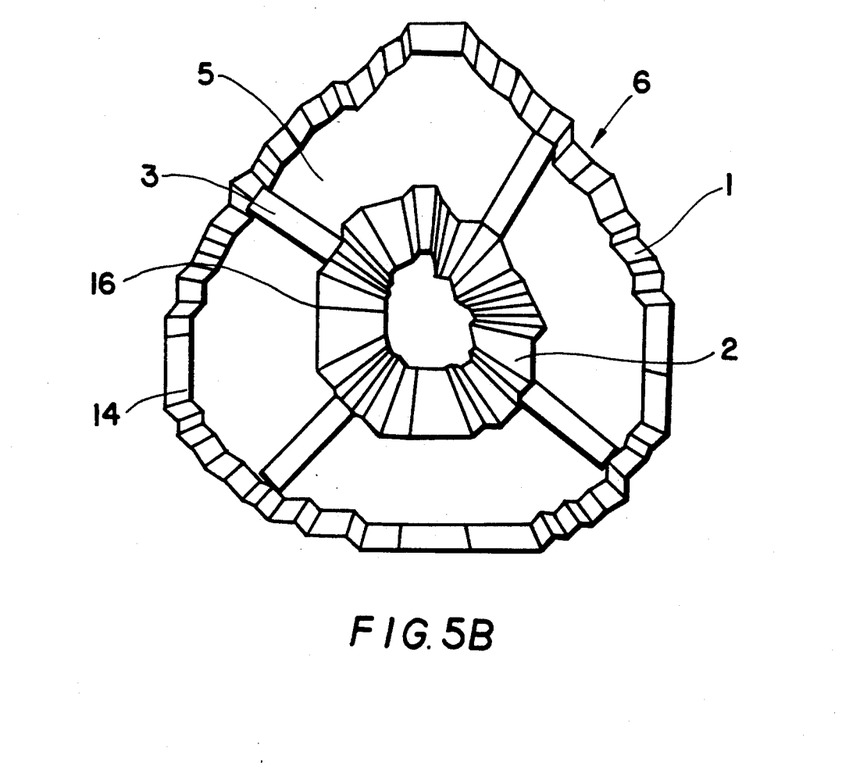

FIG. 5a shows a cross section of a femur bone 12 and FIG. 5b shows a mechanical equivalent cross section of the shell structure 6, as calculated, with the inner surface 14 of the outer shell 1 corresponding to the outer contour 15 of the femur bone 12. The outer surface 16 of the inner shell 2 corresponds to the inner contour 17 of the femur bone 12. The struts 3 connect the inner and outer shell 1 and 2 into a mechanically uniform shell structure 6 having void space 5 between the shells 1 and 2. By calculation the thicknesses of the shell walls have been optimized to make the shell structure 6 mechanically equivalent to the femur bone 12. This is done on a section-by-section basis where the data on bone can be acquired by computer tomography (CT) scans. In case of a defect, data can be collected from the contralateral bone.

Figure 6:
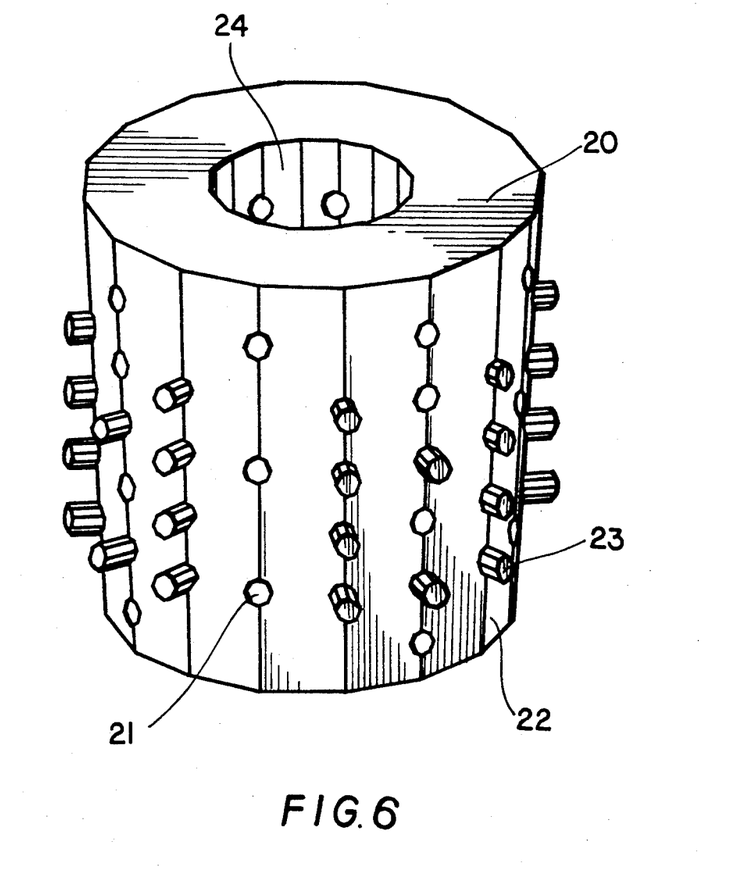
FIG. 6 shows a model used in the production of the shell structure according to FIG. 1.

In the following a method of production of a shell structure 6 according to the invention is described in detail with reference to FIGS. 6 and 7.

Anatomically shaped shell structures 6 call for special techniques of production. While a number of standard shapes can be produced by conventional techniques, the best results are obtained by custom made shell structures 6. Geometrical data can be obtained by computer tomography (CT) or magnetic resonance imaging (MRI). This may be done on the bone to be replaced, for example for planned tumor resection, or on the contralateral bone in the case of a larger defect. Based on this data a model 20 of the bone is produced as shown in FIG. 6.

A number of techniques are available for this step—the preferred one being stereolitography. This technique is fully described in U.S. Pat. No. 4,575,330 HULL.

The material of the model 20 should be water soluble and biocompatible to minimize the risks of residues on the shell structure 6. The preferred material is agar. Prior to coating the agar model 20 is freeze-dried or critical-point dried.

The model 20 contains a number of holes 21 connecting the outer surface 22 to the inner surface 24. A number of nubs 23 may extend outward from both the outer surface 22 and the inner surface 24.

Figure 7:
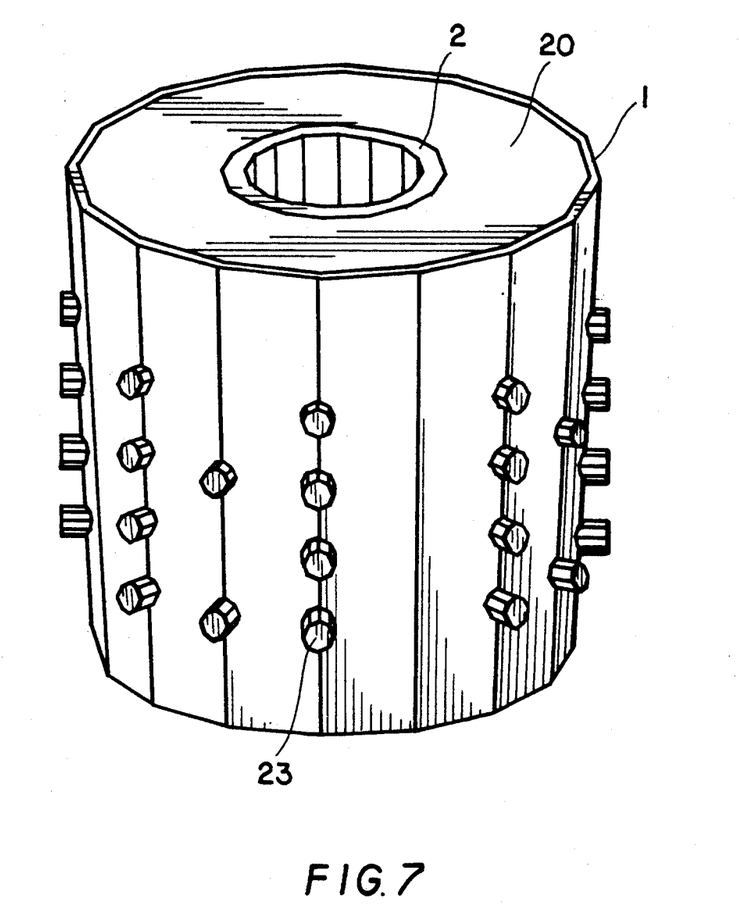
FIG. 7 shows the model of FIG. 6 coated with bioresorbable material which will remain when the water-soluble material of the model is washed away.

The model 20 is now coated by a number of layers of the shell structure material, as shown in FIG. 7. These layers will form the outer shell and the inner shell 2 of the shell structure 6. The struts 3 connecting the inner and outer shells 1 and 2 (FIG. 1) will form inside the holes 21 of the model 20 (FIG. 6). The nubs 23 can be used to control the wall thickness of the shells 1 and 2. The nubs 23 also provide the holes 4 in the inner and outer shells 1 and 2 (FIG. 1) and when the shell structure 6 is finished the model 20 is washed out by hot water leaving the shell structure 6 as represented in FIG. 1.

The preferred material for the shell structure 6 is polylactic acid (PLA) reinforced by resorbable glass fibres. The layers of material can be sprayed (in the manner of chopped fiber reinforced polyester used for boat hull manufacture) on the model 20, or the model 20 can be dip-coated. In both cases the PLA is subsequently dissolved in chloroform, or another suitable solvent. Reinforcing fibres are mixed in. High fiber loads can be achieved in this way. For example, a 5% solution of PLA in chloroform loaded with 5% fibers, will result in 50% fiber load once the solvent evaporates.

We claim:

1. A tubular shell structure for replacement of segments of long bones, having a first end and a second end for connecting first and second portions of bones, the shell structure comprising:

A) an outer tubular shell;
    B) an inner tubular shell, said inner shell being located within said outer shell and approximately parallel to said outer shell, wherein a hollow cylindrical volume is defined by a predetermined spacing between said inner shell and said outer shell structure, said volume being open at each end and fillable with living tissue or tissue precursors, said shell structure for being inserted between said first and second bone portions at said first and second ends so that said first and second bone portions correspondingly extend into said hollow cylindrical volume at said ends; and, C) a plurality of struts connecting said inner shell to said outer shell, and wherein said structure is composed of a material having an overall porosity below 90% selected from the group consisting of resorbable polymeric material, resorbable polymeric-ceramic material, degradable polymeric material and degradable polymeric-ceramic material.

2. The shell structure according to claim 1, wherein at least one of said inner and outer shell is provided with interconnected micropores.

3. The shell structure according to claim 2, wherein at least 90 percent of said micropores have a diameter below 500 μm, preferably in a range of 0.01 to 50.0 μm, most preferably in the range of 0.1 to 5.0 μm.

4. The shell structure according to claim 1, wherein at least one of said inner and outer shell is provided with larger openings in a range of 0.1 to 2.0 mm.

5. The shell structure according to claim 1, wherein said shell structure is constructed from materials selected from the group consisting of highly purified polyhydroxyacids, polysaccharides, polyamines, polyaminoacids, polyorthoesters, polyanhyrides, collagen with tricalcium phosphate and hydroxyapatite, collagen with tricalcium phosphate and bioresorbable glasses, a collagen composite with tricalcium phosphate and hydroxyapatite, and a collagen composite with tricalcium phosphate and bioresorbable glasses.

6. The shell structure according to claim 1, wherein the spacing between said inner and said outer shell is in the range of 0.1 to 10.0 mm.

7. The shell structure according to claim 1, wherein the spacing between said inner and said outer shell is in the range of 1.0 to 5.0 mm.

8. The shell structure according to claim 1, wherein said structure is reinforced with resorbable fibers.

9. The shell structure according to claim 1, wherein walls of said inner shell and said outer shell have a thickness ranging from 0.05 to 5.0 mm.

10. The shell structure according to claim 9, wherein said inner shell and said outer shell have a thickness ranging from 0.2 to 3.0 mm.

11. The shell structure according to claim 10, wherein said inner shell and said outer shell have a thickness ranging from 0.4 to 1.5 mm.

12. The shell structure according to claim 1, wherein said structure further contains antibiotic agents.

13. The shell structure according to claim 1, wherein said structure further contains antiosteomyelitis agents.

14. The shell structure according to claim 1, wherein said structure further contains antineoplastic agents.

15. The shell structure according to claim 1, wherein said structure further contains osteoconductive agents having an origin selected from the group consisting of autogenic, allogenic, xenogenic, and synthetic origins.

16. The shell structure according to claim 1, wherein said structure further contains osteoinductive agents having an origin selected from the group consisting of autogenic, allogenic, xenogenic, and synthetic origins.

17. The shell structure according to claim 1, wherein said outer shell is provided with interconnected micropores.

18. The shell structure according to claim 1, wherein said outer shell is provided with larger openings in a range of 0.1 to 2.0 mm.

* * * * *